(12) United States Patent
Taylor et al.

(10) Patent No.: US 11,083,865 B2
(45) Date of Patent: Aug. 10, 2021

(54) COMPACT PORTABLE OXYGEN CONCENTRATOR

(71) Applicant: Inogen, Inc., Goleta, CA (US)

(72) Inventors: Brenton Taylor, Kenwood, CA (US);
Peter Hansen, Santa Barbara, CA (US);
Patrick Burgess, Dunedin, FL (US);
Daniel Chin, Goleta, CA (US)

(73) Assignee: Inogen, Inc., Goleta, CA (US)

( * ) Notice: Subject to any disclaimer, the term of this patent is extended or adjusted under 35 U.S.C. 154(b) by 991 days.

(21) Appl. No.: 15/608,775

(22) Filed: May 30, 2017

(65) Prior Publication Data

US 2018/0344963 A1 Dec. 6, 2018

(51) Int. Cl.
*A61M 16/10* (2006.01)
*A61M 16/20* (2006.01)
(Continued)

(52) U.S. Cl.
CPC ...... *A61M 16/101* (2014.02); *A61M 16/0066* (2013.01); *A61M 16/085* (2014.02); *A61M 16/0858* (2014.02); *A61M 16/0875* (2013.01); *A61M 16/105* (2013.01); *A61M 16/208* (2013.01); *B01D 53/047* (2013.01); *F16K 17/0406* (2013.01); *F16K 47/08* (2013.01); *G01N 33/497* (2013.01); *A61M 16/0677* (2014.02); *A61M 2016/0027* (2013.01);
(Continued)

(58) Field of Classification Search
CPC .............. A61M 16/101; A61M 16/085; A61M 16/0858; A61M 16/0066; A61M 16/0875; A61M 16/105; A61M 16/208; A61M 16/0677; A61M 2016/0027; A61M 2019/242; A61M 2039/248; A61M 2039/2493; A61M 2202/0208; A61M 2205/0216; A61M 2205/3368; A61M 2205/502; A61M 2205/42; F16K 17/04–0413; F16K 31/0665; F16K 47/04–16; F16L 55/02; F16L 55/033–0338; G05D 507/0126–014; G05D 16/00; G05D 16/04; G05D 16/10; G05D 16/107; G05D 7/00; G05D 7/01
USPC ...................................................... 138/44–46
See application file for complete search history.

(56) References Cited

U.S. PATENT DOCUMENTS 5,161,576 A 11/1992 Hekkert et al.
5,578,115 A * 11/1996 Cole ................... B01D 53/0446
                                                                96/121
(Continued)

FOREIGN PATENT DOCUMENTS

DE   102013222368 A1 * 5/2015 ............. B60T 8/363
DE   102013222368 A1   5/2015
GB   1354239            6/1974

OTHER PUBLICATIONS

DE102013222368A1 Machine Translation (Year: 2020).*

*Primary Examiner* — Kendra D Carter
*Assistant Examiner* — Elliot S Ruddie
(74) *Attorney, Agent, or Firm* — Knobbe Martens Olson & Bear, LLP (57) ABSTRACT

Portable oxygen concentrator elements are described including integrated sensor/accumulator assemblies, new muffler designs, and improved airflow and internal gas connectivity. The result of the elements is an extremely compact, light reliable portable oxygen concentrator that is easy to assemble and relatively inexpensive.

6 Claims, 10 Drawing Sheets

(51) Int. Cl.
*F16K 47/08* (2006.01)
*B01D 53/047* (2006.01)
*F16K 17/04* (2006.01)
*A61M 16/08* (2006.01)
*A61M 16/00* (2006.01)
*G01N 33/497* (2006.01)
*A61M 16/06* (2006.01)
*A61M 39/24* (2006.01)

(52) U.S. Cl.
CPC . *A61M 2039/242* (2013.01); *A61M 2039/248* (2013.01); *A61M 2039/2493* (2013.01); *A61M 2202/0208* (2013.01); *A61M 2205/0216* (2013.01); *A61M 2205/3368* (2013.01); *A61M 2205/42* (2013.01); *A61M 2205/502* (2013.01); *B01D 2253/104* (2013.01); *B01D 2253/106* (2013.01); *B01D 2253/108* (2013.01); *B01D 2256/12* (2013.01); *B01D 2257/102* (2013.01); *B01D 2257/504* (2013.01); *B01D 2257/80* (2013.01); *B01D 2259/4533* (2013.01)

(56) References Cited

U.S. PATENT DOCUMENTS

2012/0066883 A1 3/2012 Forti
2018/0216636 A1* 8/2018 Scovell .................. F16K 47/08

* cited by examiner

COMPACT PORTABLE OXYGEN CONCENTRATOR

BACKGROUND

The specification relates to oxygen concentrators for personal use and in particular to an extremely compact portable oxygen concentrator.

Oxygen concentrators for providing oxygen rich air for therapeutic purposes are increasingly popular as alternatives to liquid oxygen vessels and compressed gas cylinders. Such personal oxygen concentrators exist in both portable form for ambulatory use and stationary form for use inside the home. To be practical for everyday use by patients needing therapeutic oxygen such portable concentrators must be small in size and weight, efficient, reliable and relatively inexpensive. These contradictory attributes may require new approaches to concentrator design.

SUMMARY

Portable oxygen concentrator elements may be provided that include integrated sensor/accumulator assemblies, new muffler designs, and improved airflow and internal gas connectivity. The result of the elements is an extremely compact, light reliable portable oxygen concentrator that is easy to assemble and relatively inexpensive.

In a first aspect, a muffler for a gas concentrator may be provided, including a pressure sensitive gas valve; and a housing made from a porous material holding the valve; wherein in the open position gas flow is substantially through an open portion of the valve, and in the closed position gas flow is directed substantially through the porous housing, muffling the sound produced by the flowing gas.

In one embodiment of the first aspect, the porous housing may be made from a sintered material. In another embodiment of the first aspect, the porous housing may be made from a multitude of individual flow channels or holes. In one embodiment of the first aspect, the pressure sensitive element may be a spring, and the pressure closing point may be set by the spring compression force. In another embodiment of the first aspect, the muffler may be placed in an exhaust outlet of a gas concentrator. In one embodiment of the first aspect, the open position flow of the valve may be substantially unrestricted. In another embodiment of the first aspect, the valve seal may be comprised from one of at least one of the following elements: a ball, a poppet, a face seal.

In a second aspect, a gas connection system for internal gas connections in a gas concentrator may be provided, including two gas ports in alignment separated by a linear or radial distance; and, a compliant, linear connector element; wherein when the two ports and the connector element are assembled, the two ports are fixed in the concentrator whereby the connector element connects the ports.

In one embodiment of the second aspect, the connector element may be made of a compliant material, including an elastomeric tube. In another embodiment of the second aspect, the connector element may contain one of a lead-in chamfer or radius to facilitate assembly. In one embodiment of the second aspect, the ports may be comprised of at least one barb. In another embodiment of the second aspect, the barb edge may be one of radiused or chamfered to facilitate removal of the tube.

In one embodiment of the second aspect, two sets of separated ports may be disposed adjacent each other in parallel, and the connector element may be a common element that is comprised of a compliant material, including an elastomeric material. In another embodiment of the second aspect, the compliant connector element may provide vibration isolation between the two ports. In one embodiment of the second aspect, the ports may overlap by length and the distance between them may be radial. In another embodiment of the second aspect, one port may be at least one end part of at least one of a removable adsorber bed inlet receptacle, and a removable adsorber bed outlet receptacle, and on the other end a port may be in fluid communication with a valve or gas flow manifold of the gas concentrator.

In a third aspect an assembly for an oxygen concentrator may be provided including an accumulator; an oxygen sensor disposed to sample gas directed to the patient gas outlet of a gas concentrator; a pressure sensor disposed to sample gas in the accumulator; a temperature sensor disposed to sample gas in the accumulator; a breath sensor disposed to sample gas at a patient gas outlet of the gas concentrator; an electronic circuit, and gas ports to the sensors and the accumulator; wherein the sensors are at least one of assembled onto an electronic circuit or directly into a body which includes the accumulator volume; and, the circuit is assembled onto the body making at least one of direct sealed gas or electrical connections to the sensors.

In one embodiment of the third aspect, the inlet ports may be connectable to a concentrator valve manifold system. In another embodiment of the third aspect, the assembly may further include at least one of a display or user interface as part of the electronic circuit. In one embodiment of the third aspect, the assembly may further include at least one of a gas output filter or cannula connection to the patient gas path, and associated inlet and outlet ports from the cannula connection to the element.

In a fourth aspect, an integrated cooling system for a portable oxygen concentrator may be provided wherein the ambient air intake is ducted to the exterior of the concentrator; the air is moved through the system by at least one fan or blower; the discharge air of the air mover is directed over at least one air compressor element; the discharge air of the air mover is directed to the intake port of at least one air compressor intake gas connection system; and the cooling air discharge vent is integrated into at least one housing panel.

In one embodiment of the fourth aspect, the air mover may be attached to the concentrator by a compliant member. In another embodiment of the fourth aspect, the compressor air intake gas may be in fluid communication with at least one vibration isolation mount of the compressor. In one embodiment of the fourth aspect, the intake gas connection system of the air compressor may be comprised of at least one substantially 90 degree bend and at least one compliant tubing member. In another embodiment of the fourth aspect, the speed of the air mover is controlled by an onboard microcontroller. In one embodiment of the fourth aspect, the speed of the air mover may be varied based on at least one system temperature measurement. In another embodiment of the fourth aspect, the system temperature measurement may be comprised of at least one of the following measurement sensors a compressor temperature sensor; an oxygen gas temperature sensor; and a circuit board temperature sensor.

BRIEF DESCRIPTION OF THE DRAWINGS

Aspects and advantages of the embodiments provided herein are described with reference to the following detailed description in conjunction with the accompanying drawings. Throughout the drawings, reference numbers may be reused to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

Personal use therapeutic oxygen concentrators are increasing in popularity, both in very small portable form and relatively small, compared to industrial gas concentrators, stationary home devices. A small portable personal use concentrator is described in co-pending application U.S. Ser. No. 15/427,948, assigned to the same assignee of the current application and incorporated in its entirety by reference, and in which the operation and use of such concentrators is described. Such concentrators because of their small size and intended personal use, have differing design considerations from large industrial concentrators intended to produce large quantities of concentrated gasses. For example, in an illustrative embodiment, the portable concentrator according to the present disclosure may be between approximately 100 and 300 cubic inches in size, between 2 and 7 pounds in weight, and may produce between 600 and 1300 ml/min of concentrated oxygen.

Figure 1:
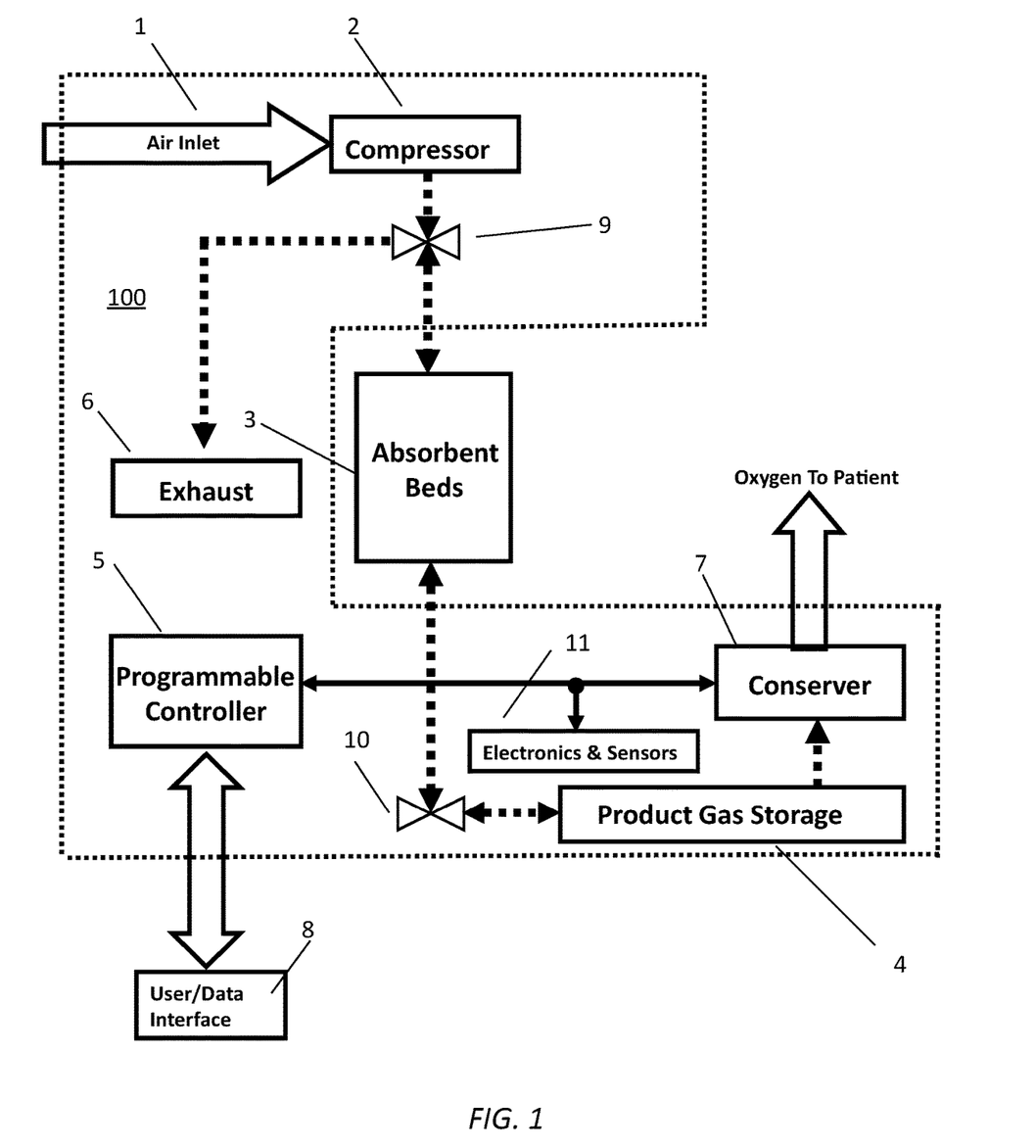
FIG. 1 shows a simplified block diagram of an exemplary portable oxygen concentrator.

FIG. 1 is directed to the components and connections for an exemplary portable oxygen concentrator 100. Air is drawn into the gas concentrator through air inlet 1 to cool the system and supply the gas separation system with ambient air for inlet and to move out the nitrogen rich exhaust gas. This air movement may be provided from a fan or blower located at the inlet, exhaust, or centrally in the air pathway. To achieve proper air flow and cooling a fan or blower in the range of 40 mm×40 mm to 100 mm×100 mm may optimally be utilized. A plurality of fans in varying sizes and locations may also be employed in some embodiments to optimize air flow and minimize noise.

The gas separation system employs pressure, vacuum, or a combination thereof in certain embodiments. Ambient air is drawn in by the compressor 2 intake through a filter and through an elongated or tortuous air path to minimize the escape of noise caused by the compressor. The compressor 2 may be comprised of a multi cylinder reciprocating piston compressor employing pressure or a combination of pressure and vacuum cylinders, but may also be comprised of multiple compressors of types including scroll, linear free piston, rotary vane, rotary screw, or diaphragm type compressors.

The pressurized air is discharged from the compressor 2 at a rate of approximately 5 SLPM to 15 SLPM per LPM of oxygen produced at a pressure up to 3 bar. The pressurized air is directed to one of two or more adsorbent beds 3 by one or more valves 9 that may be housed in a feed/waste manifold. The feed/waste valve configuration varies by embodiment and may be comprised of one or more solenoid valves, air piloted valves, rotary valves, cam actuated valves, or diaphragm valves. The feed/waste valves may be decoupled from the compressor, adsorbent beds, and other structural components to minimize transmission of noise from the valves. The valve fluid path may be connected with compliant members to achieve an appropriate level of mechanical isolation and the manifold or valve mounting is additionally isolated from other components. The feed/waste valves 9 additionally direct exhaust nitrogen gas from the adsorbent beds to a muffler in a pressure swing adsorption system or to the vacuum pump in a vacuum or pressure vacuum system.

In some embodiments, the adsorbent beds 3 are designed to be removable and replaceable as described in the above incorporated reference. Adsorbent beds may contain at least one adsorbent layer that is directed to water and carbon dioxide removal to prevent contamination of the main layer adsorbent. In some embodiments, this material may be comprised of a desiccant such as activated alumina or silica gel. In alternate embodiments, the pretreatment layer may contain a sodium or lithium exchanged zeolite. The main layer adsorbent is directed to separate oxygen from nitrogen and may be a lithium exchanged zeolite material. Nitrogen gas is retained in the adsorbent bed, while oxygen gas is allowed to pass through the adsorbent bed into the product valves 10 or product valve manifold in one embodiment.

The product valve manifold 10 may include one or more of solenoid valves, check valves, and orifices to control gas flow. The product manifold connects to the adsorbent beds and may be decoupled from the adsorbent beds and other structural components to minimize noise transmission and vibration between valves and other components in the system.

In one embodiment, oxygen gas flows from the product manifold 10 to an integrated assembly that is directed to product gas storage 4, oxygen gas concentration measurement, oxygen gas pressure sensing, as well oxygen gas filtration, and oxygen delivery, i.e. a conserver 7. In one embodiment, the integrated assembly contains multiple pressure sensors 11 for various functions including ambient pressure sensing, oxygen gas pressure measurement, and breath pressure or cannula pressure measurement.

The control of the gas concentrator is achieved by a programmable controller 5. The gas concentrator also contains a user interface 8 comprised of one or more buttons to control power state, oxygen flow rate, and additional functions.

Other embodiments additionally contain an LCD display, at least one rechargeable battery, and an integrated oxygen conserving device to deliver oxygen gas synchronously with a patient's onset of inhalation to maintain clinical efficacy while reducing the amount of oxygen gas delivered to the patient by a factor of about 2:1 to 9:1.

Figure 2:
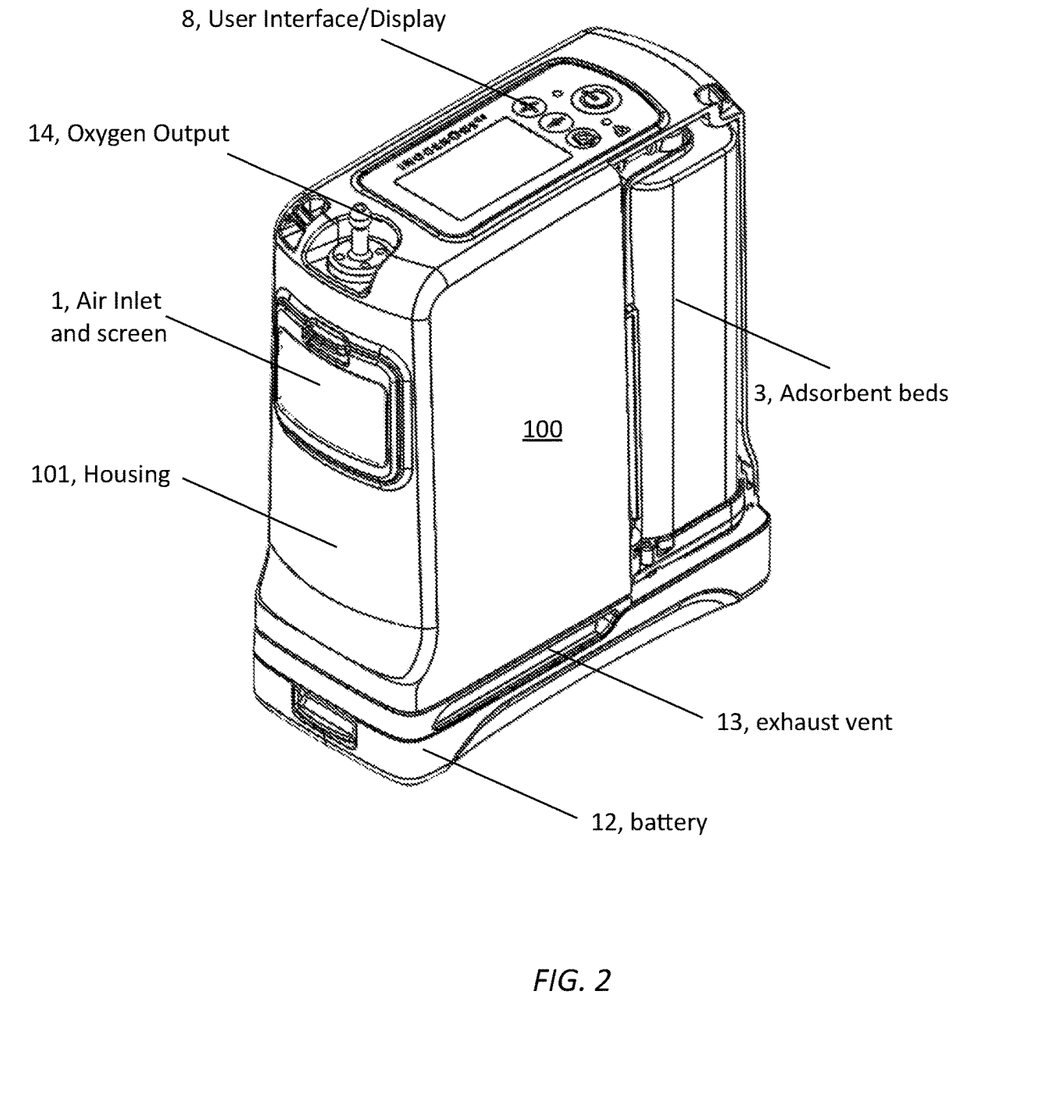
FIG. 2 shows the external layout of an exemplary portable oxygen concentrator.

FIG. 2 shows the exterior of an exemplary portable oxygen concentrator 100. Air flow enters at air inlet screen 1 and flows as described to removable adsorbent beds 3 and air exhaust 13. The gas concentrator is powered by battery 12, controlled by user interface 8, and oxygen output 14. Components of the gas concentrator are contained within housing element 101, which forms portions of the air flow path, ducting, and ventilation paths.

The embodiment of FIG. 2 is designed to be carried by an oxygen patient to supply oxygen during ambulation and is thereby designed to minimize size and weight while maximizing battery life and oxygen output. The size may be less than about 125 cubic centimeters, the weight less than about 3 pounds, and the oxygen output greater than about 630 ml/min. The oxygen output for the exemplary concentrator is actually greater than about 1.7 (ml/min oxygen)/(cm^3*lbs). This optimized oxygen output per size and weight is scalable to reach higher oxygen flow rates for patients requiring higher oxygen delivery rates at the expense of the proportionally larger size and greater weight.

Figure 3A:
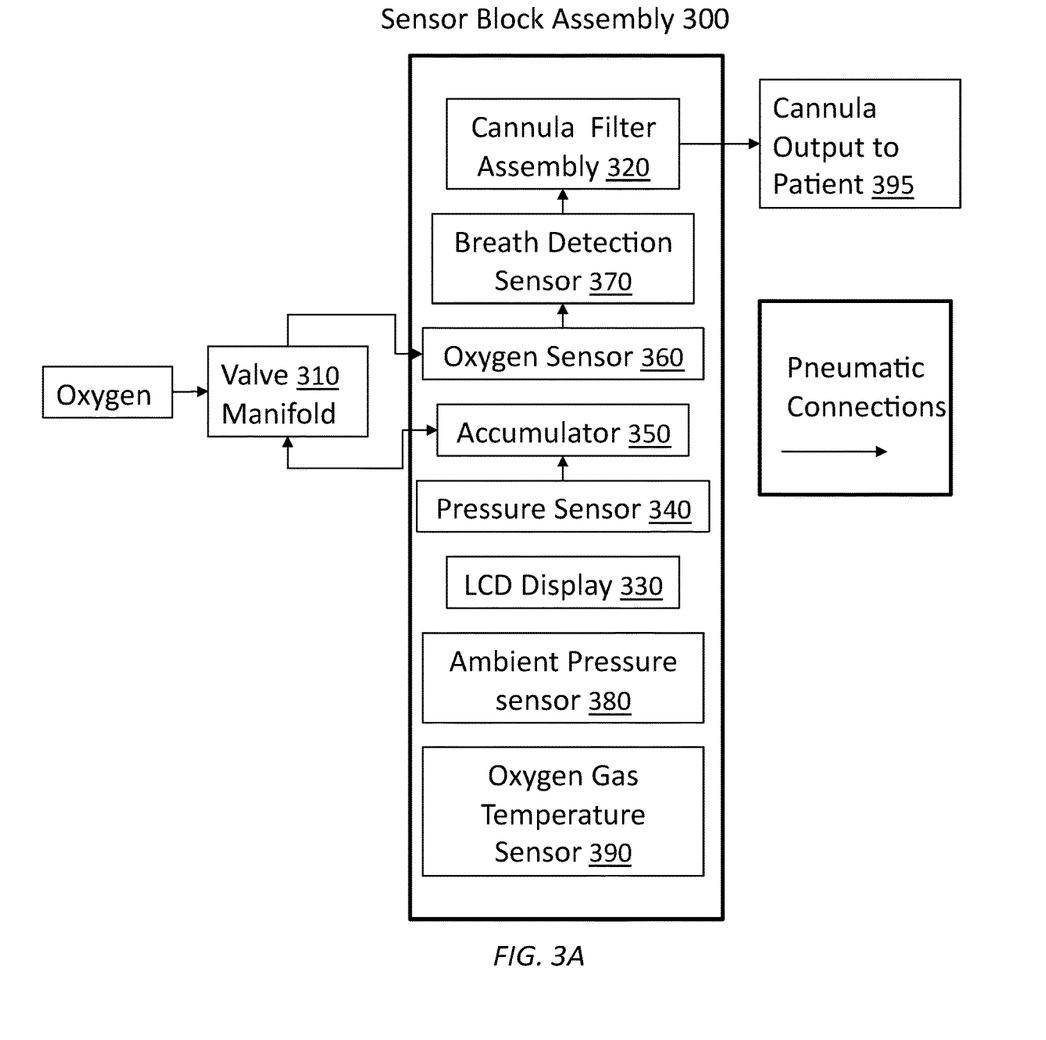
FIGS. 3A, 3B, and 3C show a block diagram and the physical layout of an illustrative embodiment of a sensor/accumulator block assembly.

FIG. 3A represents the gas flow through an embodiment of an integrated sensor block assembly 300. Oxygen gas flows from the adsorbent beds into the product valve manifold 310, filtered 320 and delivered to the patient via a cannula 395, or supplied to an adsorbent bed as purge gas. The accumulator 350 serves to buffer the production and delivery and oxygen between the PSA/VSA or other cycle and the oxygen demand from the system. The pressure swing adsorption system is controlled by the microcontroller with inputs from accumulator pressure sensor 340 to control compressor speed and valve timing to maintain target pressure ratios and operating parameters. Oxygen delivery to the patient is also controlled by the microcontroller and is dependent on inputs from breath detection sensor 370 to monitor the patient's breathing rate and onset of inhalation. The determination of the proper delivery of oxygen to the patient utilizes ambient pressure sensor 380 to correct bolus delivery for ambient pressure conditions. Oxygen concentration is monitored and via oxygen sensor 360 and oxygen gas temperature sensor 390. The temperature sensor may be located within the oxygen gas flow path in or adjacent to the oxygen sensor 360, or in the accumulator 350, or place to acquire a correlated temperature reading from circuit board 335 or other suitable location. The sensor data and signals are processed and utilized by the microcontroller to maintain proper oxygen production and delivery over a wide range of environmental conditions, required flow rates, and to compensate for changes in the system during the lifetime of the equipment.

Figure 3B:
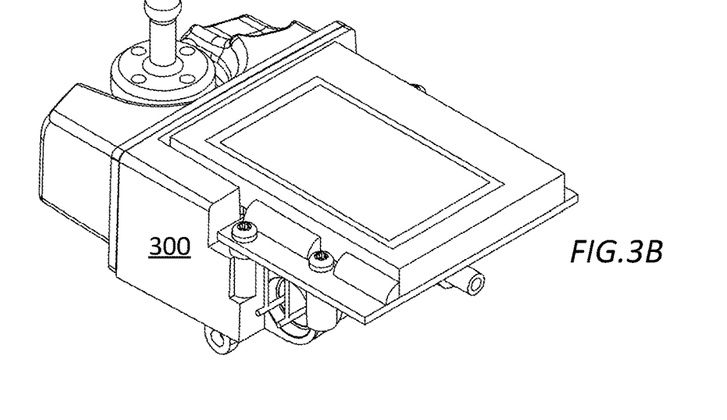

FIG. 3B depicts a particular embodiment of the integrated sensor block assembly 300.

In one embodiment, the oxygen conserver valve is an element of the product manifold. In this embodiment, the oxygen gas may flow bidirectionally between the product manifold and the sensor block assembly as it is passed through the product manifold following being produced, and then delivered to the patient passing through the oxygen conserving valve, oxygen sensor, and cannula filter assembly. The location of the conserver valve could also be chosen to have the oxygen gas delivery located entirely within the sensor block assembly 300.

Figure 3C:
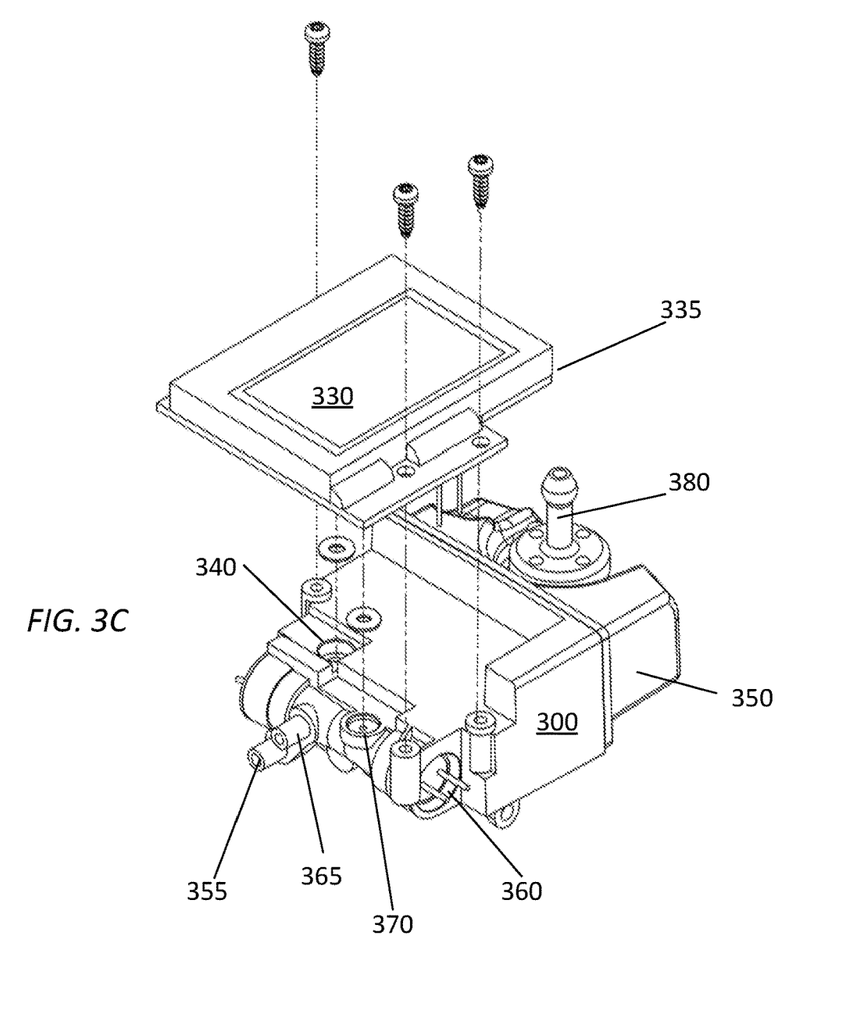

FIG. 3C is directed to an embodiment of the integrated sensor assembly 300. The volume of the assembly serves as the oxygen accumulator 350, fed by port 355, where oxygen is stored to buffer the production and delivery demands of the pressure adsorption system and the variable patient breathing rates and flow settings of the device output. In this embodiment, the pressure sensors 340, 370 and, the temperature sensor 390, and LCD display 330 are mounted to circuit board 335, wherein the pneumatic connections are made directly between the sensors and the assembly and the electrical connections are made directly between the circuit board and the pressure sensors.

Cannula output connection 380 is attached directly to the sensor assembly 300 and additionally contains a filter element to prevent any contaminants or particulates from being delivered to the patient.

Oxygen sensor 360 port 365 is designed into the integrated assembly and contains input and output connections to the product manifold that mates directly to the circuit board to measure the concentration of the of the oxygen gas. The integration of the oxygen sensor 360 and other sensors eliminates the need for multiple pneumatic connections and tubes between these components where each connection point poses a risk for assembly defects and leaks over time. Further, the integration of the circuit board 335 and LCD display 330 eliminate the need for a large number of wires and connectors since all the signals and data can be transmitted over one common connection to the microcontroller. The elimination of these individual connectors and wires reduces cost, assembly time, and risk of defects in the final product.

Figure 4A:
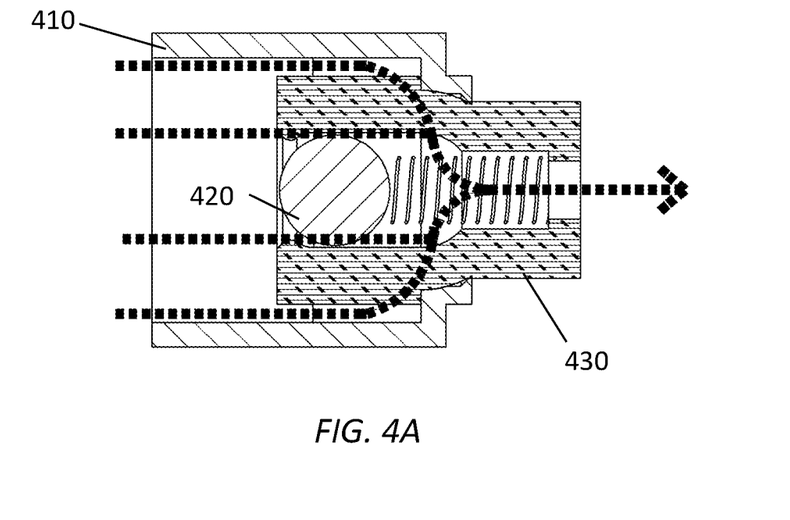
FIGS. 4A, and 4B show an illustrative embodiment of a muffler.
Figure 4B:
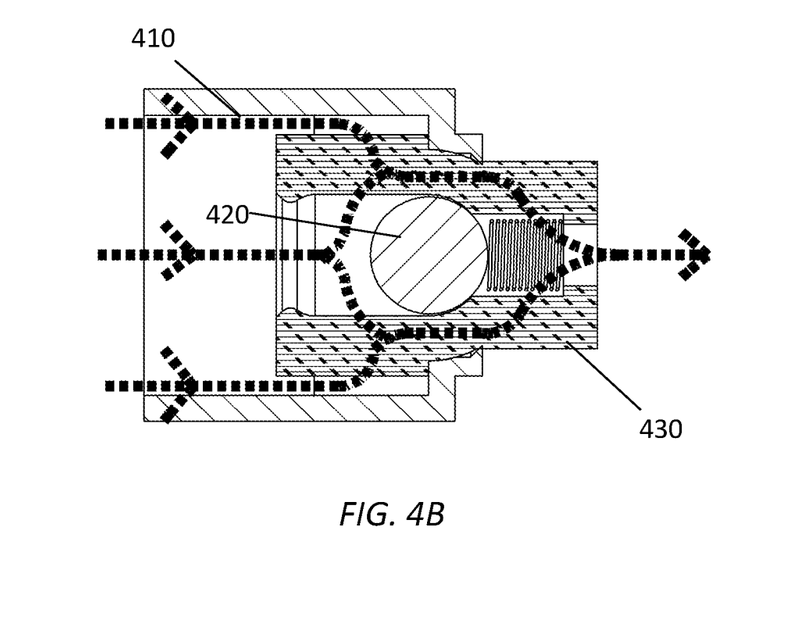

FIGS. 4A and 4B depicts an exemplary embodiment of the exhaust muffler 410. The muffler is a pressure responsive system that contains a valve 420 that opens and closes depending on the gas flow through it.

In the exemplary embodiment, the muffler body 430 is a sintered material like low density polyethylene (LDPE) or bronze. The valve 420 shown is comprised of a spring and ball wherein the high flow of nitrogen rich gas released from the adsorbent bed during the blowdown step closes the valve, FIG. 4B to force the gas through the sintered material to reduce the exhaust noise. When the high flow of gas dissipates, the spring returns the valve to the open state FIG. 4A and the low flow rate purge gas is allowed to flow directly out of the muffler without substantially passing through the sintered material. This open flow path prevents backpressure on the adsorbent bed and maximizes the efficiency of the purge and regeneration of the adsorbent material.

In alternate embodiments, the muffler material may be comprised of a perforated material, an orifice, mesh material, felt material, or other suitable material or design to control the rate of blowdown and nitrogen gas release when the valve is closed. Additionally, the pressure responsive valve may be comprised of a poppet, diaphragm, flapper, or other suitable valve design. Alternate embodiments may combine the pressure responsive element and the valve seal into one element such as a molded elastomeric valve with an inherent spring force.

FIGS. 5A, 5B, 5C and 5D show views of exemplary embodiments for a detachable gas connector system that connects an adsorbent bed receptacle to a feed/waste manifold. Each fitting 510 has a twist lock mechanism 530 to connect to a chassis portion of housing assembly 101, a radial seal mechanism to mate to an adsorbent bed receptacle, and a barbed end 560 shaped for easy tube removal and additionally containing a stop that ensures that the tube 520 is assembled to the same depth on every assembly to reduce variability and risk of leaks on the final product.

Tube 520 may be a molded elastomeric tube made from a material such as silicone, viton, EPDM, or rubber. The tube may optionally have a chamfer 540 or radius on the inner diameter to facilitate installation on to the barb or fitting. The tube may also optionally have a thickened end section 550 that ensures the tube will push onto the barb without kinking and will add additional resistance to radial expansion without adding stiffness and vibration coupling to the entire tube.

Figure 5A:
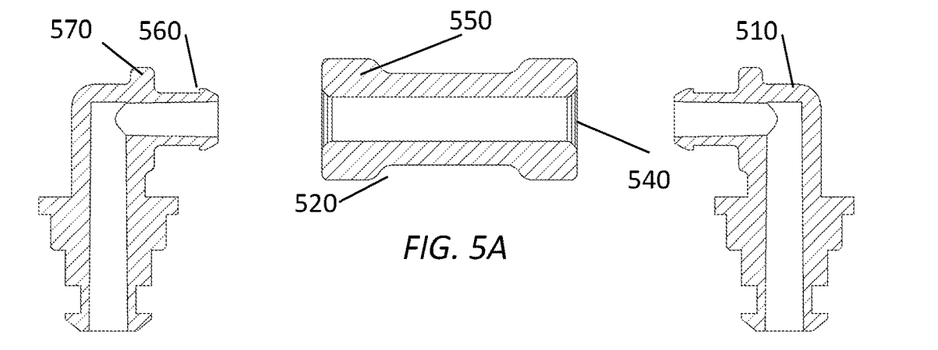
FIGS. 5A, 5B, 5C, and 5D show an illustrative embodiment of a gas interconnection element.
Figure 5B:
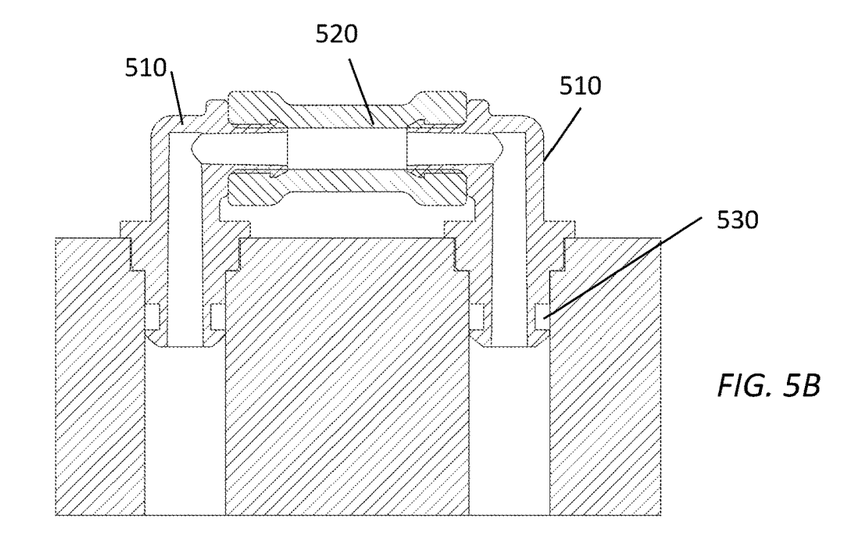

In a typical tube to barb connection, the tube/barb interface serves at least two purposes: pneumatic or hydraulic coupling as well as mechanical retention that occurs from the sharp retaining edge of the barb interfering with the tube. This connection method allows for fast, low cost connections to be made between pneumatic components. However, given the designed in mechanical interference between the tube and the barb, the tubes can often be difficult to install and often times even more difficult to remove, very often requiring destruction of the tube if removal from the barb is required. FIG. 5B depicts the gas connector system fully assembled wherein the tube 520 is constrained at each distal end to prevent the tube from detaching from the barbs and to provide precise assembly distance between the two ports and the tube. The captive ends of the tubing allow a tube to barb or fitting design that does not need to provide mechanical retention to the barb against the pressure inside the tube that would typically dislodge the tube if it were molded from a low durometer material or a thin walled design or did not have a robust mechanical interference with the barb to prevent it from detaching. The tube must only be strong enough in the radial dimension to prevent leaks caused by expansion of thickened end section 550 or by rupture of compliant tube section 520. This is facilitated by a radius at the edge of the barb at its maximum diameter where it interferes with the tube, which would normally engage the tube for mechanical retention.

When assembled, the ports of the fittings 510 are fixed in position so that the tubing creates a compliant connection between two mechanical elements, but does not lead to variability in assembly or require routing of the tubing.

Figure 5C:
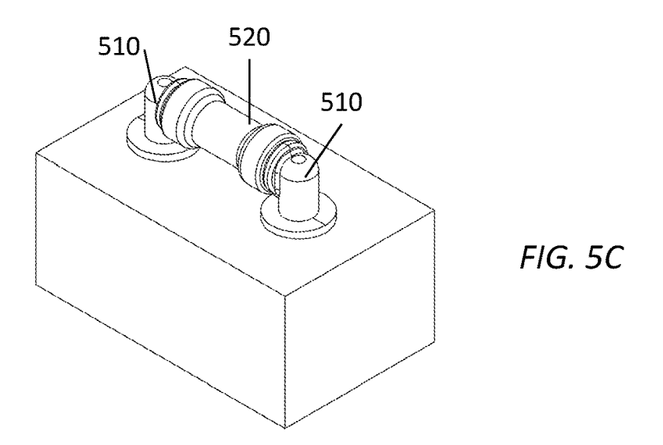
Figure 5D:
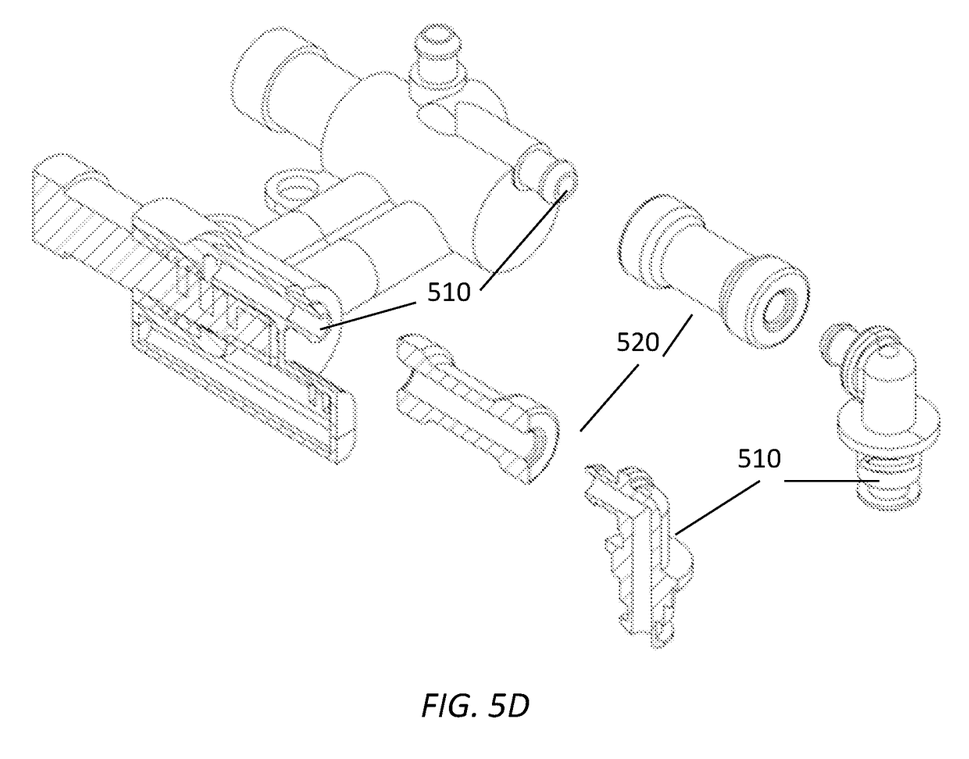

FIG. 5C is an additional example of the gas connector system directed to the fixed locations of the barb connectors and ports. FIG. 5D shows another example of such a gas connector system. In this example, one port is located on the feed/waste manifold of a gas concentrator and the other port is a fitting connected to an adsorber receptacle. The compliant tube 520 prevents noise and vibration generated by switching of the solenoid valves. The feed/waste manifold provides the mechanical support to the tube to barb connections and is affixed to posts on chassis component of housing assembly 101 via rubber grommets.

FIGS. 6A, 6B, 6C, 6D and 6E show views of exemplary embodiments of a gas connector system designed to connect a product end valve manifold to an integrated sensor assembly but may alternately be employed in various other internal gas connections within a gas concentrator.

Figure 6A:
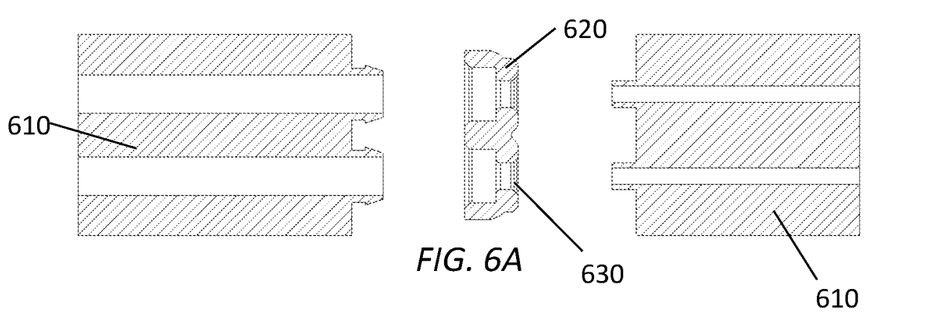
FIGS. 6A, 6B, 6C, 6D, and 6E show an alternative illustrative embodiment of a gas interconnection element.

FIG. 6A shows an exemplary exploded diagram of a gas connector system that includes two gas connections side-by-side and a common compliant sealing element.

One port 610 includes a barbed connection and the other connector is a smaller diameter straight port that allows for the ports to overlap in length to minimize space between the elements 610 while still allowing the elements to be separated by a radial distance to provide a compliant connection that minimizes transmission of noise and vibration between elements.

Figure 6B:
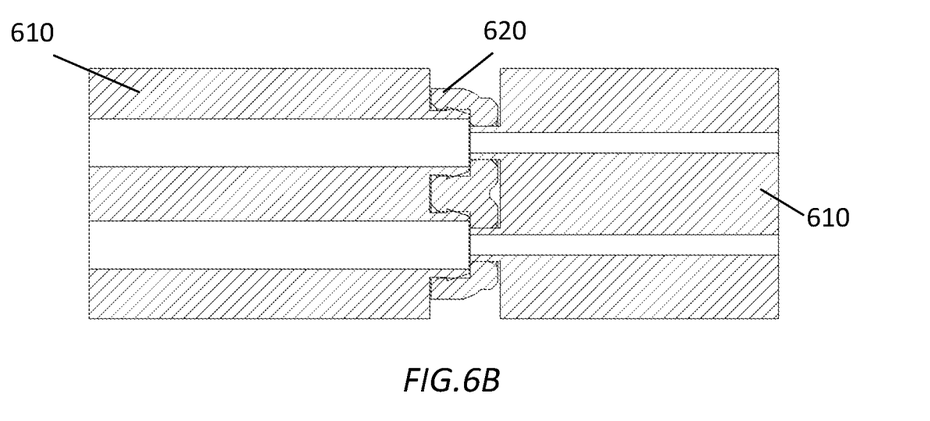

FIG. 6B depicts an exemplary embodiment of the gas connector system when it is assembled and illustrates the overlapping port lengths and captive ends of the common compliant member 620.

Compliant common member 620 may be comprised of a compliant elastomeric material such as silicone, viton, EPDM, or rubber. The compliant member may additionally contain lead-in chamfers or radiuses 630 and has ends that are captured between port elements 610 so that the tube cannot be dislodged after assembly and also ensures a repeatable position of all components.

Figure 6C:
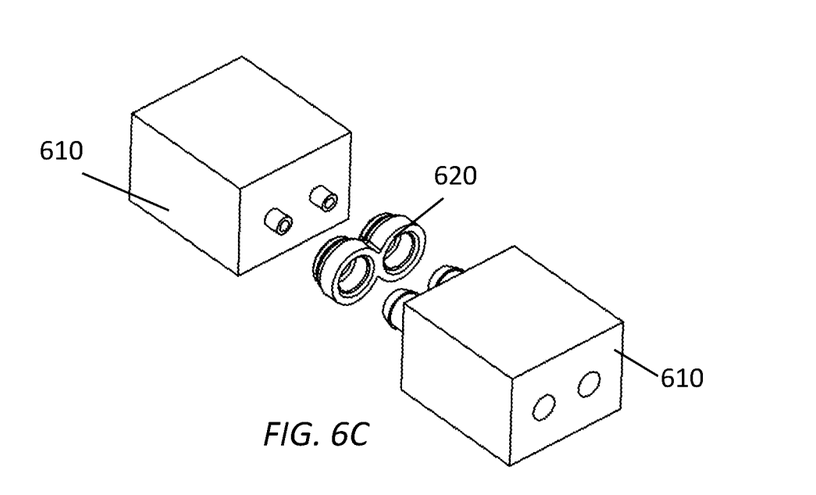
Figure 6D:
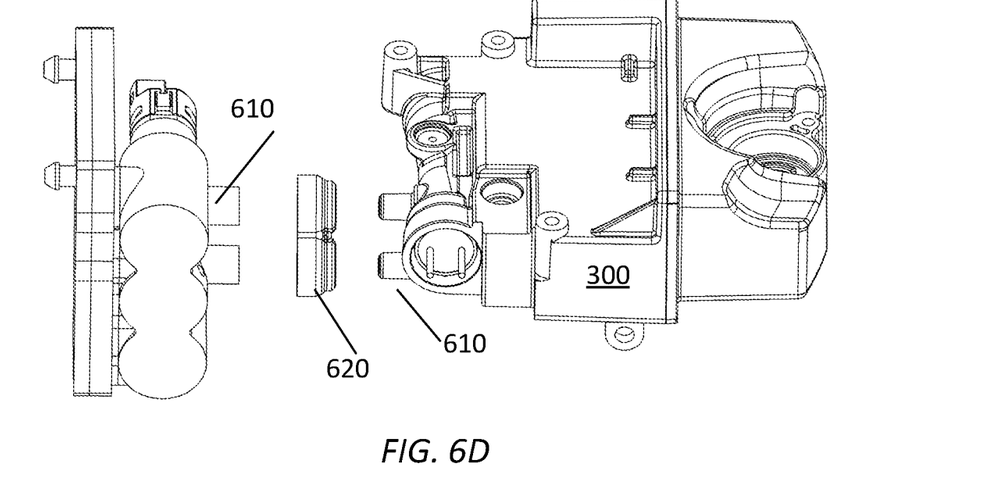
Figure 6E:
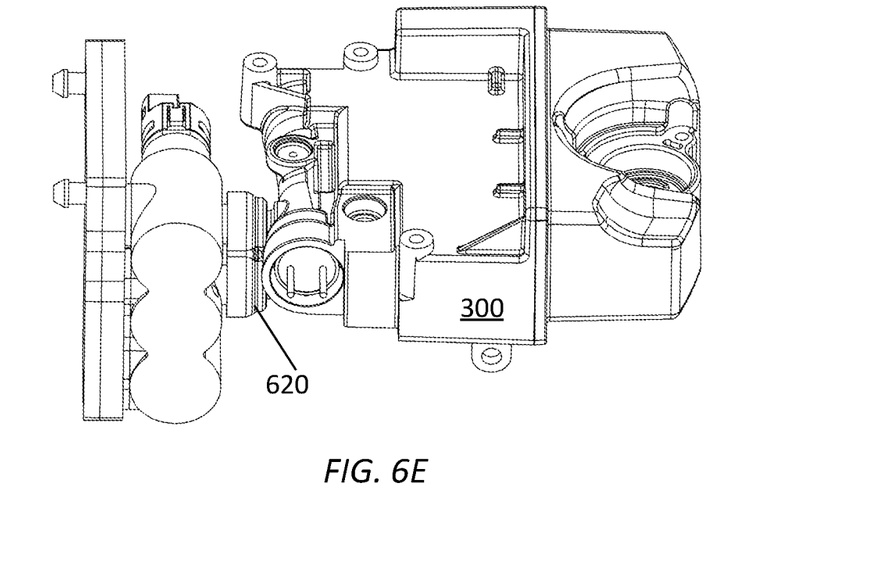

FIG. 6C shows an alternate example while FIGS. 6D and 6E show an example gas connector where one end of the connection is to integrated sensor block assembly 300 and the other end is a product valve manifold.

Figure 7:
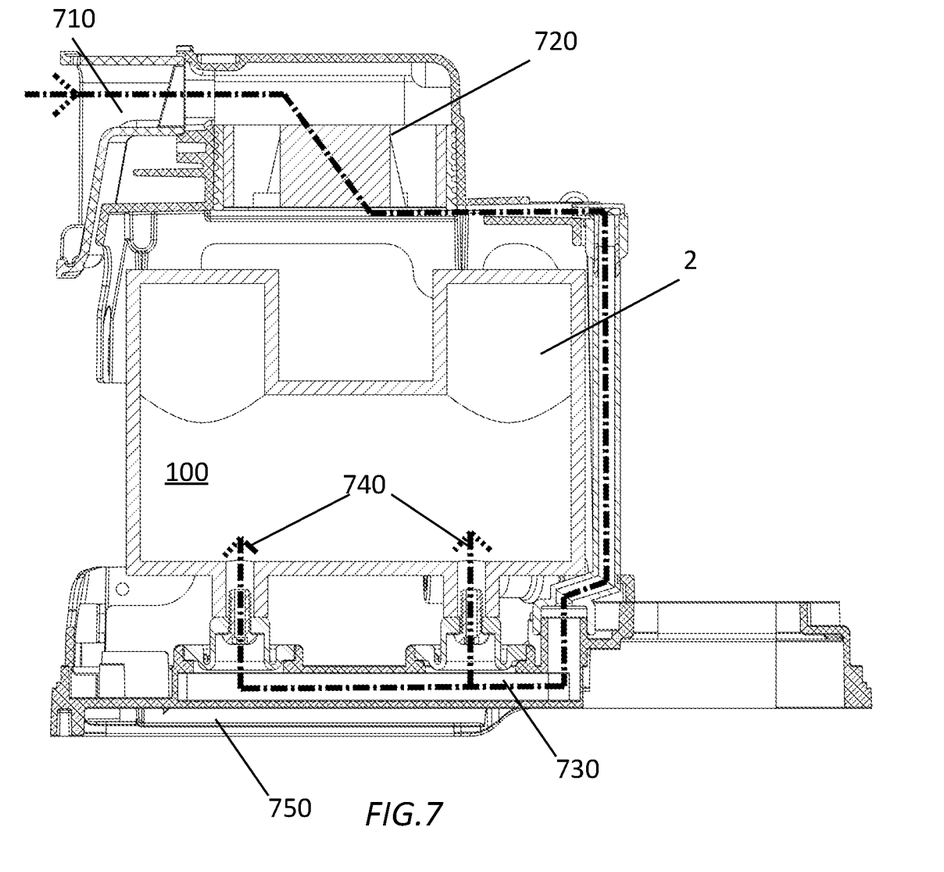
FIG. 7 shows an illustrative embodiment of internal air flow for an exemplary concentrator.

FIG. 7 is directed to the airflow through exemplary concentrator 100. Air enters through a ducted air intake 710 on the intake side of the fan 720. Ambient air passes through the fan and is discharged at a positive pressure, whereby a portion of the fan discharge air is directed to additional ducting that ports the air to the compressor intake filter 730 wherein it is filtered by passing through the filter media and directed to the compressor 2 through compliant vibration mounts and air intake ports 740.

The portion of the fan discharge air that is not directed to the compressor intake, passes over the exterior of compressor 2 and down through exhaust vents 750.

Fan discharge air may be directed to the cylinders of the reciprocating piston compressor depicted in one embodiment to maintain beneficial cooling of the piston seal moving inside the cylinder. The speed of the air mover may be varied based on the compressor speed, the accumulator pressure, or any combination of speed, pressure, and/or temperature. The rate of fan discharge may be controlled proportionally to the amount of work being done by the compressor, as measured by speed, pressure, or power. A direct measurement of compressor temperature may be made via a thermistor or a reflective temperature measurement. Alternately or additionally. the concentrator ambient temperature, the ambient temperature around the compressor or elsewhere in the concentrator, or the output gas temperature may be used. A target value for temperature that results in beneficial compressor efficiency or seal or bearing life while maintaining acceptable sound levels, or any combination thereof may be stored in the microcontroller. Discreet levels of fan speed may be stored in a lookup table based on various threshold values for any of the above values; alternatively an equation or proportional-integral-derivative control loop may be implemented.

The embodiments described herein are exemplary. Modifications, rearrangements, substitute processes, alternative elements, etc. may be made to these embodiments and still be encompassed within the teachings set forth herein. One or more of the processes described herein may be carried out by one or more processing and/or digital devices, suitably programmed.

The various illustrative processing, data display, and user interfaces described in connection with the embodiments disclosed herein can be implemented as electronic hardware, computer software, or combinations of both. To clearly illustrate this interchangeability of hardware and software, various illustrative components, blocks, and modules have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

The invention claimed is:

1. A muffler for a gas concentrator configured to direct gas through a gas separation cycle, the gas concentrator being configured to direct gas through the muffler during a high pressure flow above a threshold value and a low pressure flow below the threshold value, the muffler comprising:
 a pressure sensitive gas valve configured to transition between an open configuration and a closed configuration, the pressure sensitive gas valve configured to be in the closed configuration during the high pressure flow and configured to be in the open configuration during the low pressure flow;
 a valve channel configured to receive gas flowing through the muffler when the pressure sensitive gas valve is in the open configuration; and
 a housing made from a porous material holding the valve; wherein: the valve is configured such that gas flow is directed through the valve channel when the valve is in the open configuration, and gas flow is directed through the porous housing when the valve is in the closed configuration muffling the sound produced by the gas flow.

2. The muffler of claim 1 wherein the porous housing is made from a sintered material.

3. The muffler of claim 1 wherein the porous housing is made from a multitude of individual flow channels or holes.

4. The muffler of claim 3 wherein the valve comprises a valve seal comprising one of the following elements: a ball, a poppet, or a face seal.

5. The muffler of claim 1 wherein the valve comprises a pressure sensitive element, wherein the pressure sensitive element is a spring, and a pressure closing point is set by a spring compression force.

6. The muffler of claim 1 wherein the muffler is configured to be placed in an exhaust outlet of the gas concentrator.

* * * * *